US009958390B2

(12) United States Patent
Astier et al.

(10) Patent No.: US 9,958,390 B2
(45) Date of Patent: *May 1, 2018

(54) ON-CHIP MOLECULE FLUORESCENCE DETECTION

(71) Applicant: INTERNATIONAL BUSINESS MACHINES CORPORATION, Armonk, NY (US)

(72) Inventors: Yann Astier, Irvington, NY (US); Stephen W. Bedell, Wappingers Falls, NY (US); Ning Li, White Plains, NY (US); Devendra K. Sadana, Pleasantville, NY (US); William T. Spratt, Ossining, NY (US); Chao Wang, Chandler, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/362,259

(22) Filed: Nov. 28, 2016

(65) Prior Publication Data

US 2017/0184500 A1    Jun. 29, 2017

Related U.S. Application Data

(63) Continuation of application No. 14/982,740, filed on Dec. 29, 2015, now Pat. No. 9,513,220.

(51) Int. Cl.
*G01N 21/64* (2006.01)
*H01L 31/0216* (2014.01)
(Continued)

(52) U.S. Cl.
CPC .... *G01N 21/6428* (2013.01); *B01L 3/502707* (2013.01); *B01L 3/502715* (2013.01);
(Continued)

(58) Field of Classification Search
CPC ............. G01N 21/6428; G01N 21/645; G01N 15/1436; G01N 21/05; G01N 15/1459;
(Continued)

(56) References Cited

U.S. PATENT DOCUMENTS

| 7,221,455 B2 | 5/2007 | Chediak et al. |
| 7,511,285 B2 | 3/2009 | Bernstein |

(Continued)

FOREIGN PATENT DOCUMENTS

| JP | 2005-504293 A | 2/2005 |
| JP | 4920672 B2 | 4/2012 |
| KR | 10-2014-0098041 A | 8/2014 |

OTHER PUBLICATIONS

Mark L. Adams et al., "Microfluidic integration on detector arrays for absorption and fluorescence micro-spectrometers", 2003, Journal of Scienctific Instruments, Elsevier Science, Sensors and Acturators A, vol. 104, pp. 25-31.*

(Continued)

*Primary Examiner* — William Coleman
(74) *Attorney, Agent, or Firm* — Scully, Scott, Murphy & Presser, P.C.; Louis J. Percello, Esq.

(57) ABSTRACT

A semiconductor device used for fluorescent-based molecule detection and a method for manufacturing the same are provided. The semiconductor device has a fluid channel layer defining a fluid channel through which a sample stream flows. A target cell coupled with a fluorescent source is contained by the sample stream. The semiconductor device also has an excitation light source for generating excitation light that reaches the target cell coupled with the fluorescent source to generate fluorescent light. The semiconductor device also has a light filter layer for permitting the fluorescent light to pass through and to block the excitation light and a light detection layer for detecting the fluorescent light. The functional components of the device are highly inte- (Continued)

grated. Leakage of the excitation light and background noise into the light detection component can be minimized to improve the quality of detection.

17 Claims, 5 Drawing Sheets

(51) Int. Cl.

| | | |
|---|---|---|
| *H01L 31/0232* | (2014.01) | |
| *H01L 31/0304* | (2006.01) | |
| *H01L 25/16* | (2006.01) | |
| *H01L 31/18* | (2006.01) | |
| *H01L 31/036* | (2006.01) | |
| *G01N 15/14* | (2006.01) | |
| *G01N 21/05* | (2006.01) | |
| *B01L 3/00* | (2006.01) | |
| *G01N 15/10* | (2006.01) | |
| *G01N 15/00* | (2006.01) | |

(52) U.S. Cl.
CPC ..... *G01N 15/1436* (2013.01); *G01N 15/1459* (2013.01); *G01N 21/05* (2013.01); *G01N 21/645* (2013.01); *H01L 25/167* (2013.01); *H01L 31/02164* (2013.01); *H01L 31/02322* (2013.01); *H01L 31/036* (2013.01); *H01L 31/03044* (2013.01); *H01L 31/1856* (2013.01); *B01L 2200/12* (2013.01); *B01L 2300/168* (2013.01); *G01N 2015/0065* (2013.01); *G01N 2015/1006* (2013.01); *G01N 2021/6439* (2013.01); *G01N 2021/6471* (2013.01); *G01N 2201/062* (2013.01); *G01N 2201/06113* (2013.01); *G01N 2201/08* (2013.01)

(58) Field of Classification Search
CPC ......... H01L 31/02164; H01L 31/02322; H01L 31/03044; H01L 25/167; H01L 31/1856; H01L 31/036; B01L 3/502715; B01L 3/502707

See application file for complete search history.

(56) References Cited

U.S. PATENT DOCUMENTS

| | | |
|---|---|---|
| 7,738,086 B2 | 6/2010 | Shepard et al. |
| 8,137,626 B2 | 3/2012 | Maltezos et al. |
| 8,372,340 B2 | 2/2013 | Bird et al. |
| 8,394,642 B2 | 3/2013 | Jovanovich et al. |
| 8,541,735 B2 | 9/2013 | Foster et al. |
| 9,188,615 B2 | 11/2015 | Sturmer et al. |
| 9,194,859 B2 | 11/2015 | Emeric et al. |
| 9,513,220 B1 * | 12/2016 | Astier ................ G01N 21/6428 |
| 2004/0234417 A1 | 11/2004 | Schienle et al. |
| 2007/0059494 A1 | 3/2007 | Unger et al. |
| 2012/0070885 A1 | 3/2012 | Lenhert |
| 2012/0329040 A1 | 12/2012 | Herr et al. |
| 2013/0021789 A1 | 1/2013 | Dahm |
| 2013/0059366 A1 | 3/2013 | Pollack et al. |
| 2013/0219999 A1 | 8/2013 | Casey et al. |
| 2015/0001083 A1 | 1/2015 | Martin et al. |
| 2015/0033410 A1 | 1/2015 | Andrianov et al. |

OTHER PUBLICATIONS

Marc Dandin et al., "Optical filtering technologies for integrated fluorescence sensors", Journal of the Royal Society of Chemistry, Lab Chip, 2007, pp. 955-977.*

Hoffmann, O. et al. "Monolithically integrated dye-doped PDMS long-pass filters for disposable on-chip fluorescence detection" Lab Chip, 6:981-987 (May 2006).

Yin, D., et al. "Single-molecule detection sensitivity using planar integrated optics on a chip" Optics Letters, 31(14):2136-2138 (Jul. 2006).

List of IBM Patents or Patent Applications Treated as Related Dated Nov. 28, 2016, 2 Pages.

* cited by examiner

ON-CHIP MOLECULE FLUORESCENCE DETECTION

BACKGROUND

The present disclosure and embodiments thereof are in the field of a semiconductor device and more particularly, to semiconductor devices used for fluorescence-based molecule detection and analysis.

Fluorescent-based molecule detection and analysis is commonly used for medical purpose, in which a target molecule is labeled with a fluorophore molecule to cause the target molecule to be fluorescent. A fluorescent-based molecule detection system typically includes an excitation light source, which emits excitation light to the labeled target molecule to cause the fluorophore molecule to emit fluorescent light. The fluorescent light is subsequently focused and collected by a light detector of the system, which can be a charge-coupled device (CCD) or a photomultiplier tube (PMT). An optical filter is typically provided to the system to improve the signal-to-noise ratio (SNR) by removing the reflected excitation light and/or background light.

Conventional fluorescent-based molecule detection systems suffer certain deficiencies. First, the excitation light source is not formed integrally with the other parts of the system, particularly the light detector, through a semiconductor manufacturing process to allow fast and easy production of detection systems in a mass scale. Furthermore, conventional fluorescent-based molecule detection systems do not achieve satisfactory separation of the fluorescent light from the excitation light. Consequently, certain excitation light may leak into the light detector, which deteriorates the quality of detection.

Accordingly, there exists a need in the art to overcome the deficiencies and limitations described hereinabove with respect to conventional fluorescent-based molecule detection systems.

SUMMARY

In one aspect of the present application, a semiconductor device used for fluorescent-based molecule detection is provided. The semiconductor device includes a fluid channel layer defining a fluid channel. The fluid channel has an inlet for admitting a sample stream and an outlet for discharging the sample stream, wherein the sample stream includes at least one target cell coupled with a fluorescent source. The semiconductor device further includes an excitation light source for generating excitation light. The excitation light reaches the target cell coupled with the fluorescent source to generate fluorescent light. The semiconductor device also includes a light filter layer configured to permit the fluorescent light to pass through and to block the excitation light, and a light detection layer coupled to the light filter layer and configured to detect the fluorescent light.

In another aspect of the present application, a method for manufacturing a semiconductor device used for fluorescent-based molecule detection is provided. The method includes forming a light detection layer on a substrate, wherein the light detection layer is configured to detect fluorescent light; forming a light filter layer on the light detection layer, wherein the light filter layer is configured to permit the fluorescent light to pass through and to block excitation light; forming a fluid channel layer on the light filter layer for defining a fluid channel, wherein the fluid channel has an inlet for admitting a sample stream and an outlet for discharging the sample stream, wherein the sample stream includes at least one target cell coupled with a fluorescent source; forming an excitation light source for generating excitation light, wherein the excitation light reaches the target cell coupled with the fluorescent source to generate the fluorescent light; and bonding the excitation light source onto the fluid channel layer.

In yet another aspect of the present application, a method for manufacturing a semiconductor device used for fluorescent-based molecule detection is provided. The method includes forming an excitation light source on a substrate for generating excitation light, wherein the excitation light reaches a target cell coupled with a fluorescent source to generate fluorescent light; forming a light detection layer on the substrate, wherein the light detection layer is configured to detect the fluorescent light; forming an optical spacer on the substrate, wherein the optical spacer is interposed between the excitation light source and the light detection layer for preventing the excitation light from entering the light detection layer; forming a light filter layer on the light detection layer, wherein the light filter layer is configured to permit the fluorescent light to pass through and to block the excitation light, wherein a top surface of the light filter layer and a top surface of the optical spacer are coplanar to provide a first uniform top surface; forming a light guiding layer on the first uniform top surface for deflecting the excitation light from the excitation light source, wherein a top surface of the light guiding layer and a top surface of the excitation light source are coplanar to provide a second uniform top surface; and forming a fluid channel layer on the second uniform surface for defining a fluid channel, wherein the fluid channel has an inlet for admitting a sample stream and an outlet for discharging the sample stream, wherein the sample stream includes the target cell coupled with the fluorescent source.

DETAILED DESCRIPTION OF EMBODIMENTS

The present application will now be described in greater detail by referring to the following discussion and drawings that accompany the present application. It is noted that the drawings of the present application are provided for illustrative purposes only and, as such, the drawings are not drawn to scale. It is also noted that like and corresponding elements are referred to by like reference numerals.

In the following description, numerous specific details are set forth, such as particular structures, components, materials, dimensions, processing steps and techniques, in order to provide an understanding of the various embodiments of the present application. However, it will be appreciated by one of ordinary skill in the art that the various embodiments of the present application may be practiced without these specific details. In other instances, well-known structures or processing steps have not been described in detail in order to avoid obscuring the present application.

Figure 1:
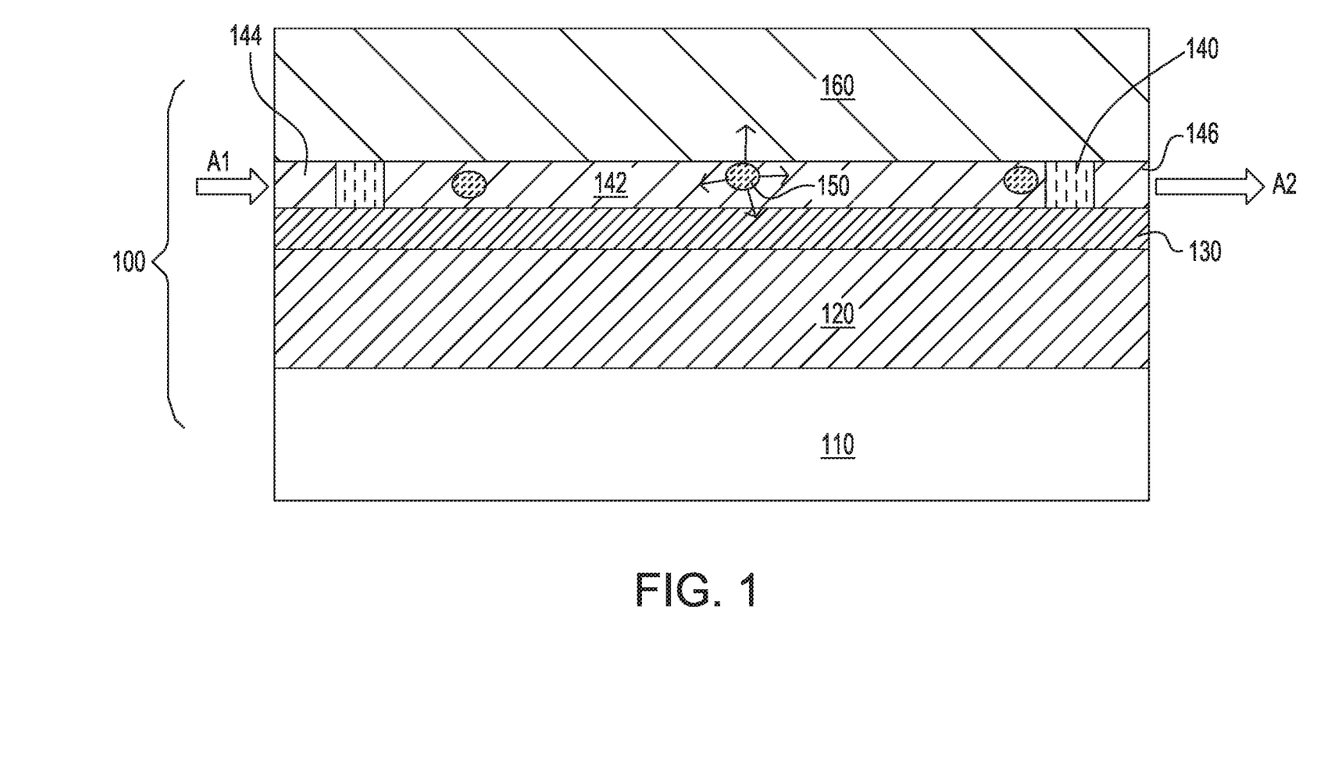
FIG. 1 is a cross sectional view of a semiconductor device in accordance with a first exemplary embodiment of a first aspect of the present application.

FIG. 1 shows a cross section view of a semiconductor device 100 used for fluorescent-based molecule detection, according to an exemplary embodiment of the present application.

The semiconductor device 100 includes a substrate 110. The substrate 110 may include a semiconductor material such as, for example, silicon (Si), germanium (Ge), a silicon germanium (SiGe) alloy, a silicon carbide (SiC) alloy, a silicon germanium carbide (SiGeC) alloy, or a III/V compound semiconductor (e.g., InAs, GaAs or InP). In another embodiment of the present application, the substrate 100 may be an organic multilayer laminate or PCB. In yet another embodiment of the present application, the substrate 110 may comprise a dielectric material such as, for example, undoped glass or doped glass. In yet another embodiment of the present application, the substrate 100 may comprise a metal such as, for example, titanium (Ti), vanadium (V), chromium (Cr), manganese (Mn), iron (Fe), cobalt (Co), nickel (Ni), copper (Cu), molybdenum (Mo) and alloys, oxides and nitrides thereof.

The semiconductor device 100 also includes a light detection layer 120 formed on the substrate 110. The light detection layer 120 can be a CCD (charge-coupled device) array, a photodetector array or a photomultiplier tube, which is capable of receiving and detecting fluorescent light. The light detection layer 120 can also be any suitable semiconductor array, such as, a Si detector array. A light filter layer 130 is formed on the light detection layer 120 and is configured to permit the fluorescent light to pass through and block excitation light. The light filter layer 130 can also be configured to block any background noise. For example, the light filter layer 130 can be a dichroic mirror coating formed on the light detection layer 120.

The semiconductor device 100 further includes a fluid channel layer 140 formed on the light filter layer 130. The fluid channel layer 140 defines therein a microfluidic channel 142. The microfluidic channel 142 has inlet 144 for admitting a sample stream flowing into the fluid channel layer 140 in direction A1. The microfluidic channel 142 also has an outlet 146 for discharging the sample stream flowing out of the fluid channel layer 140 in direction A2. The sample stream includes therein at least one target cell 150, which is coupled with a fluorescent source (not shown), such that when excitation light is incident onto the target cell 150, fluorescent light is generated accordingly. The fluorescent light can be detected by the light detection layer 120 for sampling and analyzing the target cell 150 for medical purposes. The fluid channel layer 140 can be formed by depositing a dielectric layer, such as, a $SiO_2$ layer, onto the top surface of the light filter layer 130 and subsequently, etching the dielectric layer to provide the microfluidic channel 142.

The semiconductor device 100 also includes an excitation light source 160 for generating excitation light. For example, the excitation light source 160 can be any suitable III-V based LED panel or layer, such as, a GaN based LED panel, a GaAs based LED panel and an InGaN based LED panel. Alternatively, the excitation light source 160 can also be a laser source. The excitation light source 160 can be fabricated individually and subsequently bonded onto the top of the fluid channel layer 140.

When the semiconductor device 100 is used for conducting a fluorescent-based molecule detection, the sample stream is introduced into the microfluidic channel 142 through the inlet 144. As the sample stream flows to the outlet 146 of the microfluidic channel 142, the excitation light source 160 is energized to generate excitation light, which is projected into the microfluidic channel 142 and incident onto the fluorescent-labeled target cell 150 to generate fluorescent light. The fluorescent light passes through the light filter layer 130 to be detected by the light detection layer 120. Simultaneously, the excitation light is deflected or optimally, blocked by the light filter layer 130, thereby preventing noise from entering the light detection layer 120.

The semiconductor device 100 provides a highly integrated fluorescent-based molecule detection mechanism, which is structurally compact and can be easily manufactured through a semiconductor process suitable for mass production. More importantly, the optical signals, which are considered noise for molecule detection, can be effectively deflected or blocked to improve the performance of the semiconductor device 100.

Figure 2:
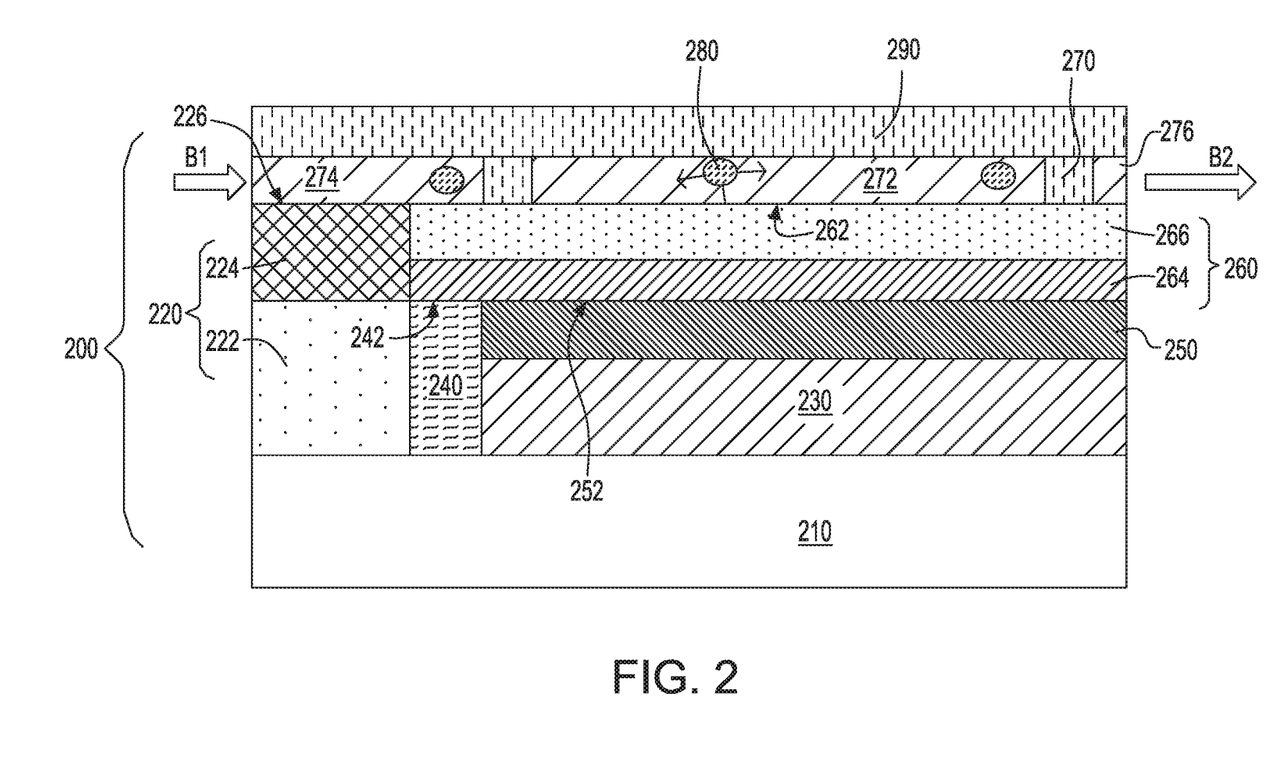
FIG. 2 is a cross sectional view of a semiconductor device in accordance with a second exemplary embodiment of a first aspect of the present application.

FIG. 2 shows a cross section view of a semiconductor device 200 used for fluorescent-based molecule detection, according to another exemplary embodiment of the present disclosure.

The semiconductor device 200 includes a substrate 210. The substrate 210 may comprise a semiconductor material such as, for example, silicon (Si), germanium (Ge), a silicon germanium (SiGe) alloy, a silicon carbide (SiC) alloy, a silicon germanium carbide (SiGeC) alloy, or a III/V compound semiconductor (e.g., InAs, GaAs or InP). In another embodiment of the present application, the substrate 210 may be an organic multilayer laminate or PCB. In yet another embodiment of the present application, the substrate 210 may comprise a dielectric material such as, for example, undoped glass or doped glass. In yet another embodiment of the present application, the substrate 210 may comprise a metal such as, for example, titanium (Ti), vanadium (V), chromium (Cr), manganese (Mn), iron (Fe), cobalt (Co), nickel (Ni), copper (Cu), molybdenum (Mo) and alloys, oxides and nitrides thereof.

An excitation light source 220 is formed on the substrate 210. In this embodiment, the excitation light source 220 includes a buffer layer 222 formed on the substrate 210 and an excitation light layer 224 formed on the buffer layer 222. The excitation light layer 224 can be any suitable III-V based LED panel or a laser source. A light detection layer 230 is formed on the substrate 210 and spaced from the excitation light source 220. The light detection layer 230 can be a CCD array, a photodetector array or a photomultiplier tube, which is capable of receiving and detecting fluorescent light. The light detection layer 230 can also be any suitable semiconductor array, such as, a Si detector array.

An optical spacer 240 is also formed on the substrate 210 and interposed between the excitation light source 220 and the light detection layer 230, for preventing the excitation light generated by the excitation light source 220 from entering the light detection layer 230. A light filter layer 250 is formed on the light detection layer 230. The light filter layer 250 can the same or similar as the light filter layer 130 of the semiconductor device 100. The optical spacer 240 has a top surface 242 and the light filter layer 250 has a top surface 252. The top surface 242 of the optical spacer 240 and the top surface 252 of the light filter layer 250 are coplanar to provide a first uniform top surface 242/252.

A light guiding layer 260 is formed on the first uniform top surface 242/252. The light guiding layer 260 is configured to guide the excitation light generated by the excitation light source 220 in a horizontal direction as indicated by arrow H shown in FIG. 2, the detail of which will be explained later. The light guiding layer 260 has a top surface 262 and the excitation light source 220 has a top surface 226. The top surface 262 of the light guiding layer 260 and the top surface 226 of the excitation light source 220 are coplanar to provide a second uniform top surface 262/226. A fluid channel layer 270 is formed on the second uniform top surface 262/226, for defining therein a microfluidic channel 272. The microfluidic channel 272 has inlet 274 for admitting a sample stream flowing into the fluid channel layer 270 in direction B1. The microfluidic channel 272 also has an outlet 276 for discharging the sample stream flowing out of the fluid channel layer 270 in direction B2. The sample stream includes therein at least one target cell 280, which is coupled with a fluorescent source (not shown), such that when the excitation light is incident onto the target cell 280, fluorescent light is generated accordingly. The fluorescent light can be detected by the light detection layer 230 for sampling and analyzing the target cell 280 for medical purposes. The fluid channel layer 270 can be formed by depositing a dielectric layer, such as, a $SiO_2$ layer, onto the second uniform top surface 262/226 and subsequently, etching the dielectric layer to provide the microfluidic channel 272. A top glass layer 290 can be bonded to the fluid channel layer 270.

The light guiding layer 260 includes a relatively low index dielectric layer 264 formed on the second uniform top surface 262/226 and a relatively high index dielectric layer 266 formed on the relatively low index dielectric layer 264. Specifically, the relatively high index layer has a refractive index that is a few percent (such as, one to nine percent) to a few times (such as, one to nine times) higher than the relatively low index layer. The relatively low index dielectric layer 264 and the relatively high index dielectric layer 266 together define an interface 268 of index contrast. When the excitation light in the relatively high index dielectric layer 266 is incident onto the interface 268, majority of the excitation light is reflected by the interface 268 back to the relatively high index dielectric layer 266. As a result, the excitation light, which moves downwardly toward the light detector layer 230, can be effectively "trapped" in the relatively high index dielectric layer 266. Ultimately, the majority of the excitation light is deflected upwardly toward the fluid channel layer 270, and also horizontally in the direction of arrow H from a side of the light guiding layer 260 adjacent to the excitation light source 220 to an opposite side of the light guiding layer 260 distal of the excitation light source 220. Specifically, the light is trapped in the relatively high index layer due to confined propagating optical mode, which can be also viewed as total internal reflection.

The semiconductor device 200 provides a highly integrated fluorescent-based molecule detection mechanism, which is structurally compact and can be easily manufactured through a semiconductor process suitable for mass production. In addition, the semiconductor device 200 can effectively minimize leakage of the excitation light into the light detection layer and at the same time, properly guide the excitation light into the fluid channel layer.

Figure 3:
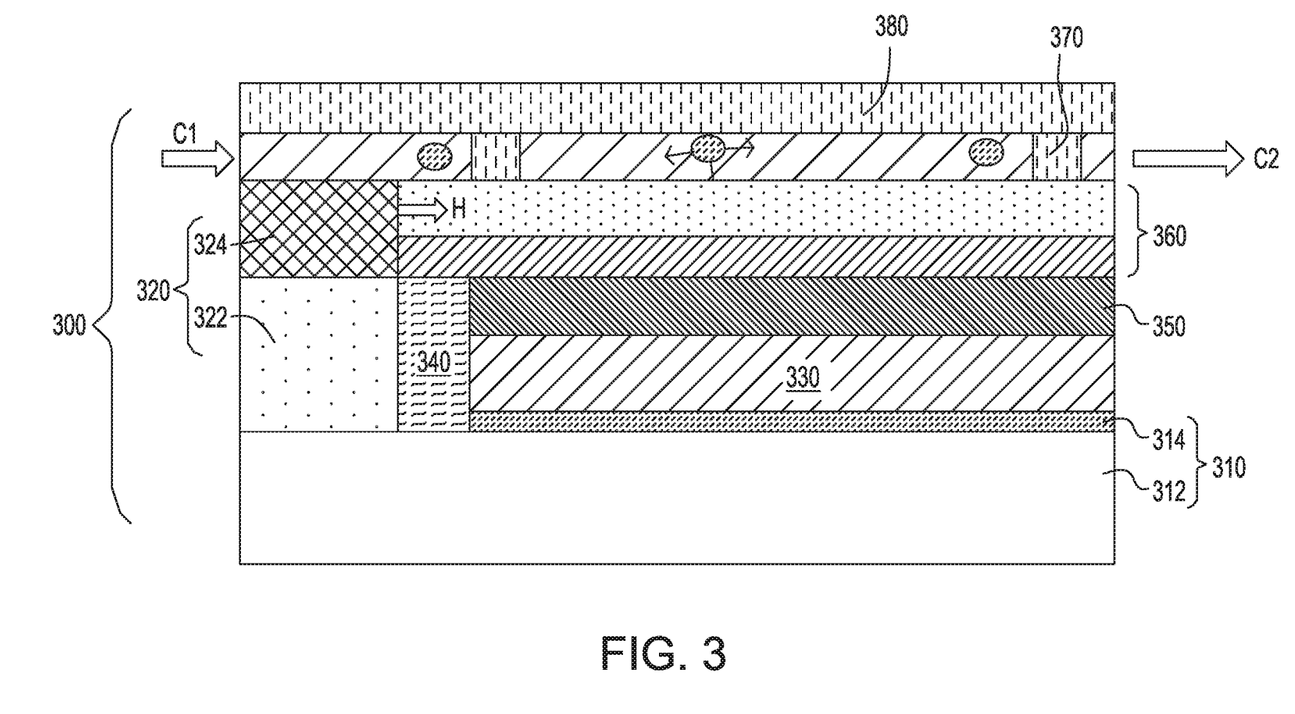
FIG. 3 is a cross sectional view of a semiconductor device in accordance with a third exemplary embodiment of a first aspect of the present application.

FIG. 3 shows a cross section view of a semiconductor device 300 used for fluorescent-based molecule detection, according to yet another exemplary embodiment of the present disclosure.

The semiconductor device 300 includes a substrate 310, an excitation light source 320 formed on the substrate 310, a light detection layer 330 formed on the substrate 310, and an optical spacer 340 formed on the substrate 310 and interposed between the excitation light source 320 and the light detection layer 330. The excitation light source 320 includes a buffer layer 322 formed on the substrate 310 and an excitation light layer 324 formed on the buffer layer 322. The semiconductor device 300 also includes a light filter layer 350, a light guiding layer 360, a fluid channel layer 370 and a top class layer 380. The above elements of the semiconductor device 300 can be same or similar as the counterpart elements of the semiconductor device 200. Therefore, description of these elements of the semiconductor device 300 is omitted for brevity.

The substrate 310 of the semiconductor device 300 is a Silicon-On-Insulator (SOI) substrate, which includes a Si substrate 312 of a {111} crystal orientation and an insulator layer 314 formed on the Si substrate 312. In this embodiment, the light detection layer 330 is formed on a top surface of the insulator layer 314, while the excitation light source 320 and the optical spacer 340 are formed on a top surface of the Si substrate 312, which achieves an improved isolation of light detection layer 330 from the excitation light source 320 and also makes it easier to form the light detection layer 330 on the insulator layer 314. In addition, the semiconductor device 300 is capable of achieving all the benefits of the semiconductor device 200 as described above.

Figure 4:
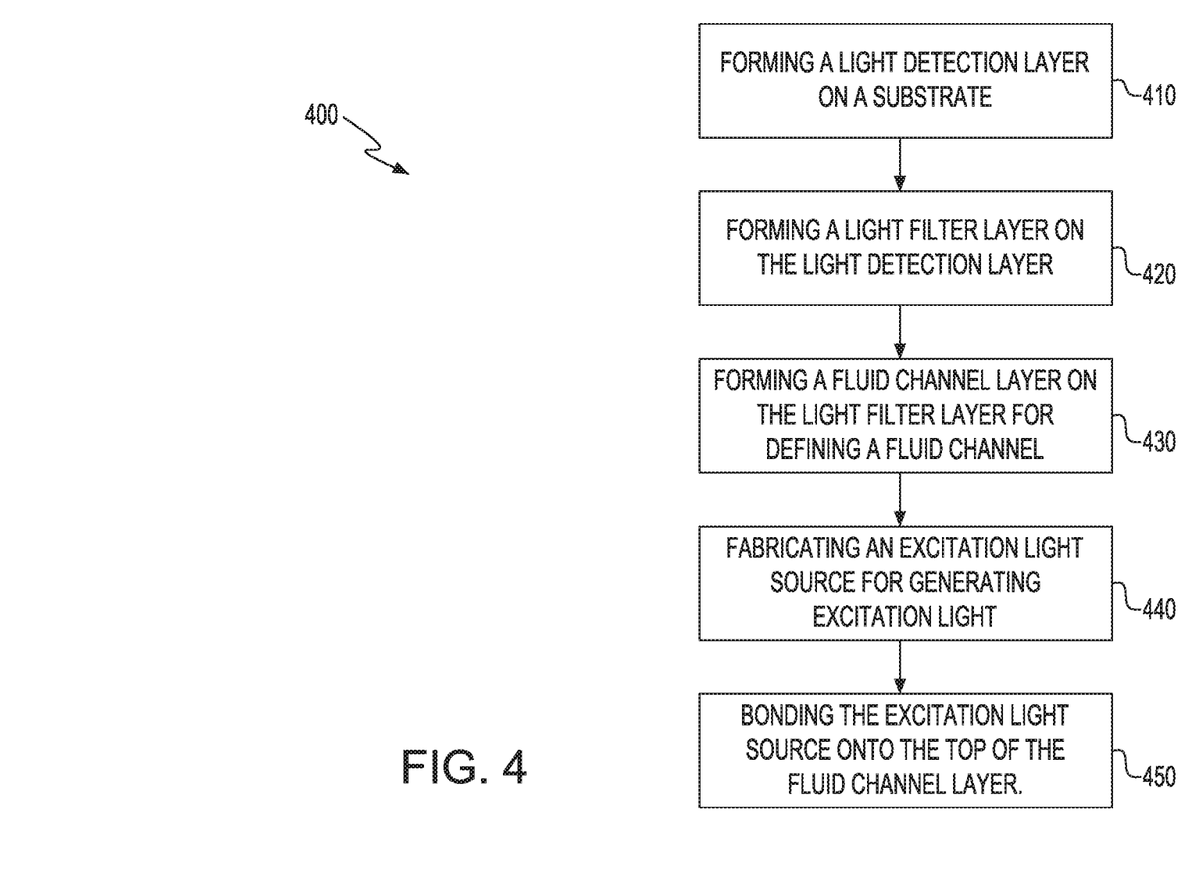
FIG. 4 is a flow chart of a process for manufacturing a semiconductor device in accordance with a first exemplary embodiment of a second aspect of the present application.

FIG. 4 is a flow chart showing a method 400 for manufacturing a semiconductor device used for fluorescent-based molecule detection, according to an exemplary embodiment of another aspect of the present disclosure. The method 400 can be used to fabricate the semiconductor device 100 as describe above. At step 410, a light detection layer, which is configured to detect fluorescent light, is formed on a substrate. The light detection layer can be formed by fabricating Si detector arrays on the substrate. At step 420, a light filter layer is formed on the light detection layer, for example, by depositing a dielectric filter layer on the light detection layer. The light filter layer is configured to permit the fluorescent light to pass through and to block excitation light. At step 430, a fluid channel layer is formed on the light filter layer for defining a fluid channel. The fluid channel has an inlet for admitting a sample stream and an outlet for discharging the sample stream. The sample stream contains at least one target cell coupled with a fluorescent source. For example, the fluid channel layer can be formed by depositing a $SiO_2$ layer on the light filter layer and subsequently etching the $SiO_2$ layer to provide the fluid channel. At step 440, an excitation light source for generating the excitation light is fabricated, which emits excitation light to the target cell coupled with the fluorescent source to generate the fluorescent light. The excitation light source can include a III-V based LED panel, such as a GaN based LED panel, a GaAs based LED panel or an InGaN based LED panel. At step 450, the excitation light source is bonded onto the top of the fluid channel layer.

Figure 5:
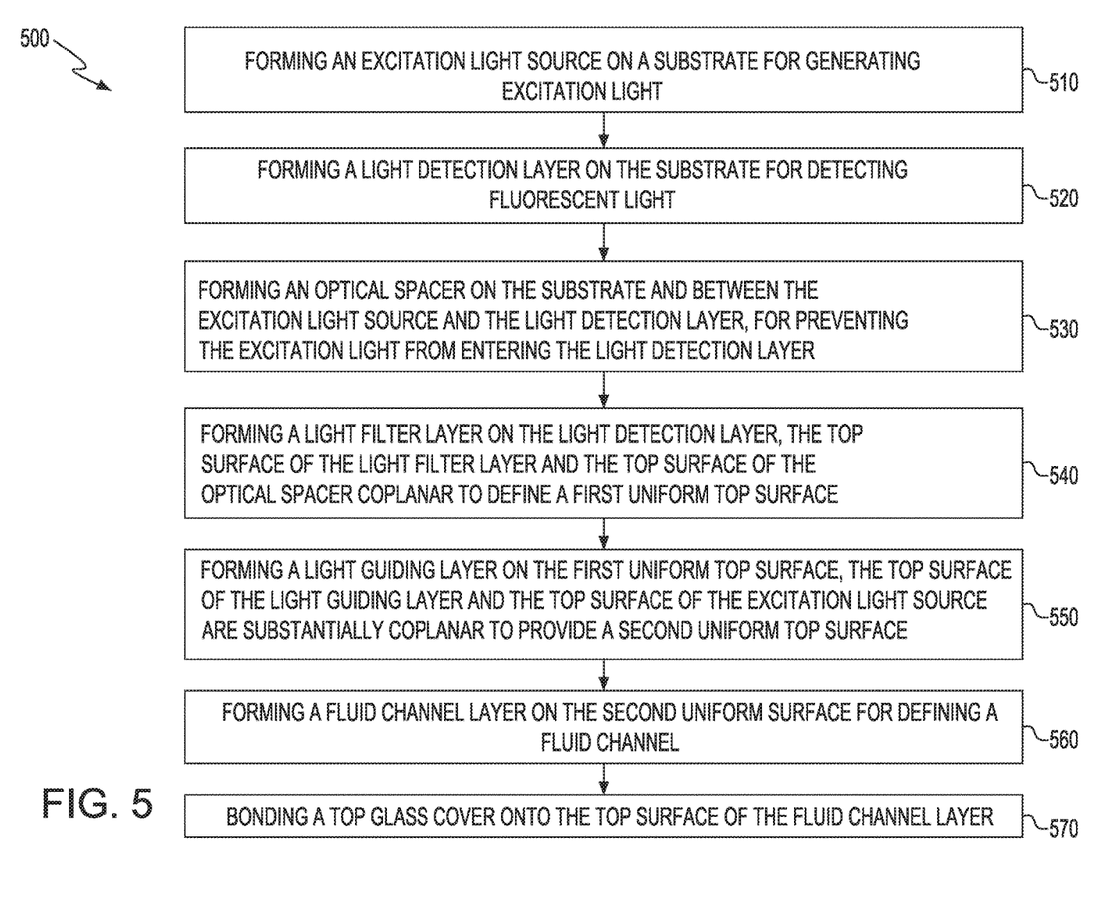
FIG. 5 is a flow chart of a process for manufacturing a semiconductor device in accordance with a second exemplary embodiment of a second aspect of the present application.

FIG. 5 is a flow chart showing a method 500 for manufacturing a semiconductor device used for fluorescent-based molecule detection, according to an exemplary embodiment of another aspect of the present disclosure. The method 500 can be used to fabricate the semiconductor device 200 or 300 as described above.

At step 510, an excitation light source is formed on a substrate for generating excitation light. The excitation light reaches a target cell coupled with a fluorescent source to generate fluorescent light. For example, trenches can be formed on the substrate and one or more III-V based light emitting diodes can be grown and patterned on the trenches. Alternatively, a laser source can be formed on the substrate. The excitation light source can be formed to have a buffer layer on the substrate.

At step 520, a light detection layer is formed on the substrate for detecting the fluorescent light. The light detection layer can be formed by fabricating Si detector arrays on the substrate. This step can be implemented prior to or after step 510. Optionally, the substrate is a Silicon-On-Insulator (SOI) substrate that includes a Si substrate of a {111} crystal orientation and an insulator layer on the Si substrate, in which case the light detection layer is formed on the insulator layer.

At step 530, an optical spacer is formed on the substrate. The optical spacer is interposed between the excitation light source and the light detection layer for preventing the excitation light from entering the light detection layer.

At step 540, a light filter layer is formed on the light detection layer. The light filter layer is configured to permit the fluorescent light to pass through and to block the excitation light. A top surface of the light filter layer and a top surface of the optical spacer are formed coplanar to provide a first uniform top surface.

At step 550, a light guiding layer is formed on the first uniform top surface for deflecting the excitation light from the excitation light source. A top surface of the light guiding layer and a top surface of the excitation light source are coplanar to provide a second uniform top surface. The light guiding layer can be formed by depositing a relatively low index dielectric layer on the first uniform surface and depositing a relatively high index dielectric layer on the relatively low index dielectric layer.

At step 560, a fluid channel layer is formed on the second uniform surface for defining a fluid channel. The fluid channel has an inlet for admitting a sample stream and an outlet for discharging the sample stream. The sample stream contains the target cell coupled with the fluorescent source. The fluid channel layer can be formed by depositing a $SiO_2$ layer on the second uniform surface and etching the $SiO_2$ layer to provide the fluid channel.

At step 570, a top glass cover is bonded onto the top surface of the fluid channel layer.

According to the semiconductor device used for fluorescent-based molecule detection as described above, all functional components of the device are highly integrated to provide a compact unit. In addition, satisfactory separation of the fluorescent light from excitation light and background noise can be achieved, and leakage of the excitation light and the background noise into the light detection component can be minimized to improve the quality of detection.

While the present application has been particularly shown and described with respect to various embodiments thereof, it will be understood by those skilled in the art that the foregoing and other changes in forms and details may be made without departing from the spirit and scope of the present application. It is therefore intended that the present application not be limited to the exact forms and details described and illustrated, but fall within the scope of the appended claims.

What is claimed is:

1. A semiconductor device comprising:
   a fluid channel layer defining a fluid channel, wherein the fluid channel has an inlet for admitting a sample stream and an outlet for discharging the sample stream, wherein the sample stream comprises at least one target cell coupled with a fluorescent source;
   an excitation light source for generating excitation light, wherein the excitation light reaches the target cell coupled with the fluorescent source to generate fluorescent light;
   a light filter layer configured to permit the fluorescent light to pass through and to block the excitation light; and
   a light detection layer coupled to the light filter layer and configured to detect the fluorescent light.

2. The semiconductor device of claim 1, wherein the excitation light source comprises at least one of a III-V based LED panel and a laser source, wherein the III-V based LED panel comprises at least one of a GaN based LED panel, a GaAs based LED panel and an InGaN based LED panel.

3. The semiconductor device of claim 1, wherein the fluid channel layer comprises a $SiO_2$ layer.

4. The semiconductor device of claim 1, wherein the light filter layer has a top surface, wherein the light filter layer comprises a dichroic mirror coating located on the light detection layer.

5. The semiconductor device of claim 4, wherein the fluid channel layer is located on the top surface of the light filter layer and the excitation light source is located on the fluid channel layer.

6. The semiconductor device of claim 4,
   wherein the excitation light source is located on the top surface of a substrate and having a top surface; and further comprising:
   an optical spacer located on the top surface of the substrate, wherein the optical spacer is interposed between the excitation light source and the light detection layer for preventing the excitation light from entering the light detection layer, wherein the optical spacer has a top surface that is coplanar with the top surface of the light filter layer to provide a first uniform top surface; and
   a light guiding layer located on the first uniform top surface for deflecting the excitation light from the excitation light source into the fluid channel of the fluid channel layer, wherein the light guiding layer has a top surface;
   wherein the top surface of the excitation light source is coplanar with the top surface of the light guiding layer to provide a second uniform top surface; and
   wherein the fluid channel layer is formed on the second uniform top surface.

7. The semiconductor device of claim 6, further comprising a top glass cover located on the fluid channel layer.

8. The semiconductor device of claim 6, wherein the excitation light source comprises a buffer layer formed on the top surface of the substrate.

9. The semiconductor device of claim 6,
   wherein the light guiding layer comprises a first dielectric layer disposed on the first uniform surface and a second dielectric layer disposed on the first dielectric layer;
   wherein the first dielectric layer has a first refractive index and the second dielectric layer has a second refractive index different than the first refractive index; and
   wherein the first dielectric layer and the second dielectric layer together define an interface of index contrast for guiding the excitation light from a side of the light guiding layer adjacent to the excitation light source to an opposite side of the light guiding layer.

10. A method for manufacturing a semiconductor device, said method comprising:

forming a light detection layer on a substrate, wherein the light detection layer is configured to detect fluorescent light;

forming a light filter layer on the light detection layer, wherein the light filter layer is configured to permit the fluorescent light to pass through and to block excitation light;

forming a fluid channel layer on the light filter layer for defining a fluid channel, wherein the fluid channel has an inlet for admitting a sample stream and an outlet for discharging the sample stream, wherein the sample stream comprises at least one target cell coupled with a fluorescent source;

forming an excitation light source for generating the excitation light, wherein the excitation light reaches the target cell coupled with the fluorescent source to generate the fluorescent light; and bonding the excitation light source onto the fluid channel layer.

11. The method of claim 10, wherein the forming the fluid channel layer on the light filter layer comprises depositing a $SiO_2$ layer on the light filter layer and etching the $SiO_2$ layer to provide the fluid channel.

12. The method of claim 10, wherein the forming the excitation light source comprises forming at least one of a III-V based LED panel and a laser source, wherein the III-V based LED panel comprises at least one of a GaN based LED panel, a GaAs based LED panel and an InGaN based LED panel.

13. A method for manufacturing a semiconductor device, said method comprising:

forming an excitation light source on a substrate for generating excitation light, wherein the excitation light reaches a target cell coupled with a fluorescent source to generate fluorescent light;

forming a light detection layer on the substrate, wherein the light detection layer is configured to detect the fluorescent light;

forming an optical spacer on the substrate, wherein the optical spacer is interposed between the excitation light source and the light detection layer for preventing the excitation light from entering the light detection layer;

forming a light filter layer on the light detection layer, wherein the light filter layer is configured to permit the fluorescent light to pass through and to block the excitation light, wherein a top surface of the light filter layer and a top surface of the optical spacer are coplanar to provide a first uniform top surface;

forming a light guiding layer on the first uniform top surface for deflecting the excitation light from the excitation light source, wherein a top surface of the light guiding layer and a top surface of the excitation light source are coplanar to provide a second uniform top surface; and forming a fluid channel layer on the second uniform surface for defining a fluid channel, wherein the fluid channel has an inlet for admitting a sample stream and an outlet for discharging the sample stream, wherein the sample stream comprises the target cell coupled with the fluorescent source.

14. The method of claim 13, wherein the forming the fluid channel layer on the second uniform surface comprises depositing a $SiO_2$ layer on the second uniform surface and etching the $SiO_2$ layer to provide the fluid channel.

15. The method of claim 13, wherein the forming the excitation light source comprises forming at least one of a III-V based LED panel and a laser source, wherein the III-V based LED panel comprises at least one of a GaN based LED panel, a GaAs based LED panel and an InGaN based LED panel.

16. The method of claim 13, wherein the forming the light guiding layer on the first uniform top surface comprises depositing a first dielectric layer having a first refractive index on the first uniform surface and depositing a second dielectric layer having a second refractive index on the first dielectric layer, wherein the first refractive index is different than the second refractive index, and wherein the first dielectric layer and the second dielectric layer together define an interface of index contrast for guiding the excitation light from a side of the light guiding layer adjacent to the excitation light source to an opposite side of the light guiding layer.

17. The method of claim 13, wherein the forming the excitation light source on the substrate comprises forming a buffer layer on the substrate and an excitation light layer on the buffer layer.

* * * * *